United States Patent
Bager et al.

(10) Patent No.: US 7,572,492 B2
(45) Date of Patent: Aug. 11, 2009

(54) METHOD FOR WELDING COMPONENT OF A MULTI-LAYER CONSTRUCTION

(75) Inventors: Kim Bager, Lyngby (DK); Ingrid Læsøe Fink, Rødovre (DK); Thorkild Vorm, Holte (DK)

(73) Assignee: Coloplast A/S, Humlebaek (DK)

( * ) Notice: Subject to any disclaimer, the term of this patent is extended or adjusted under 35 U.S.C. 154(b) by 205 days.

(21) Appl. No.: 11/826,266

(22) Filed: Jul. 13, 2007

(65) Prior Publication Data
US 2007/0262479 A1  Nov. 15, 2007

Related U.S. Application Data

(62) Division of application No. 10/297,930, filed on Dec. 19, 2002, now Pat. No. 7,244,482.

(51) Int. Cl.
| | |
|---|---|
| B29D 22/00 | (2006.01) |
| B29D 23/00 | (2006.01) |
| B32B 1/08 | (2006.01) |
| B32B 27/32 | (2006.01) |
| B23Q 5/22 | (2006.01) |
| B23K 3/06 | (2006.01) |

(52) U.S. Cl. ............... 428/35.2; 428/35.7; 428/35.9; 428/53; 228/244

(58) Field of Classification Search ............ 428/35.2, 428/35.7, 34.1, 35.9, 53; 623/11.11; 219/121.64; 228/244
See application file for complete search history.

(56) References Cited

U.S. PATENT DOCUMENTS

| | | | |
|---|---|---|---|
| 4,636,609 A | 1/1987 | Nakamata | |
| 4,847,462 A | 7/1989 | Soodak et al. | |
| 5,165,799 A | 11/1992 | Wood | |
| 2002/0005246 A1 | 1/2002 | Van Vliet et al. | |

FOREIGN PATENT DOCUMENTS

| | | |
|---|---|---|
| DE | 44 32 081 A1 | 3/1996 |
| DE | 198 14 298 A1 | 10/1999 |

(Continued)

OTHER PUBLICATIONS

XP-0-00952346; "Jones et al.," Use of Infrared Dyes for Transmission Laser Welding of Plastics; Abtec, Conference Proceedings, 2000; 1166-1170.

*Primary Examiner*—Michael C Miggins
(74) *Attorney, Agent, or Firm*—Jacobson Holman PLLC

(57) ABSTRACT

A method for welding together two layers or workpieces within a multi-layer assembly in which laser light is directed through an outer layer of the assembly, allowing transmission of the laser light from its outer surface to at least within the vicinity of its inner surface substantially without any absorption of energy from the laser light. The laser light is directed towards a layer having an absorbent component, corresponding to a portion thereof, capable of absorbing laser light within a given wavelength range thereby creating a welded area between a surface of the layer having the absorbent component and a surface of a layer facing the layer having the absorbent component. The absorbent component can be provided either within the bulk of a layer or it can be provided as a separate surface layer on one or both surfaces of a layer.

36 Claims, 5 Drawing Sheets

FOREIGN PATENT DOCUMENTS

| | | |
|---|---|---|
| DE | 198 32 168 A1 | 1/2000 |
| EP | 0 045 587 A1 | 2/1982 |
| EP | 0 087 403 A1 | 8/1983 |
| EP | 0 106 587 A2 | 4/1984 |
| EP | 0 158 528 A2 | 10/1985 |
| EP | 0 483 569 A1 | 5/1992 |
| EP | 0 942 139 A1 | 9/1999 |
| EP | 0 997 261 A1 | 5/2000 |
| HU | P0002500 | 11/2000 |
| HU | P0203827 | 3/2003 |
| HU | P0300624 | 7/2003 |
| JP | 62 71626 A | 4/1987 |
| WO | WO 93/17643 | 9/1993 |
| WO | WO 95/26869 | 10/1995 |
| WO | WO 99/02330 | 1/1999 |
| WO | WO 00/03865 | 1/2000 |
| WO | WO 00/20157 | 4/2000 |
| WO | WO 01/44357 A1 | 6/2001 |
| WO | WO 01/82846 A1 | 11/2001 |

METHOD FOR WELDING COMPONENT OF A MULTI-LAYER CONSTRUCTION

RELATED APPLICATIONS

This application is a divisional application of application Ser. No. 10/297,930 filed Dec. 19, 2002, issued as U.S. Pat. No. 7,244,482 on Jul. 17, 2007, and hereby claims the priority thereof to which it is entitled.

The present invention relates to methods for welding together two layers, or work-pieces, within a multi-layer assembly. More specifically, but not exclusively, the present invention relates to a method for the manufacture of medical devices comprising a plurality of layers interconnected by welded joints or seams. Typically, the materials for such devices are thin, flexible polymer foils or sheets used for producing bag-like containers. The invention also relates to specific products manufactured using the inventive concept of the present invention.

BACKGROUND OF THE INVENTION

In the past, different methods have been used for welding sheet-like materials together, for example traditional heat contact welding. In this method the two sheets to be welded together are placed or clamped between a heated welding element and a support element such that the sheets are pressed against each other with a given force to ensure close contact between the surfaces to be welded. Heat is then applied from one side through one of the sheets until, by heat transfer, it reaches the second sheet; typically materials are chosen such that both materials will melt and a weld will be established between the two sheets. This method necessitates free access to both sides of the two-layer assembly.

A different method used is HF welding in which the two sheets to be welded together are placed or clamped between a support element and an element from which a radio frequency signal is directed into the layers, this resulting in "internal" heating of the materials. Due to radiation from the surfaces of the materials to be welded, heat build-up is strongest towards the centre of the two-layer assembly which, when the layers have the same thickness, is also the location for the area to be welded, i.e. the contacting surfaces. Drawbacks of this method are that the materials must be sensitive to HF, e.g. PVC. The materials and the HF process are generally environmentally hazardous, and the difficulties associated with welding materials with different thickness limit the applications.

A further method is laser welding using a $CO_2$ laser which tends to heat most plastics from the surface down with a very rapid heating action being achievable; in this way it resembles traditional heat transfer welding. Nd:YAG and diode laser light will transmit through un-pigmented polymers. The polymer can be designed to absorb and heat in these laser beams due to inherent properties or with the addition of an absorber. This process was first described in 1985 for welding automotive components; see Japanese patent application JP85-213304 "Laser beam welding of plastic plates" published Sep. 26, 1985 and known as transmission laser welding. Typically carbon black pigment is used as the additive to enhance absorption from transmission laser welding, however, carbon black, which results in a black material when added, is traditionally considered unsuitable for medical use in which a transparent appearance is in most cases desirable. It is also possible to use materials which are opaque instead of black; however, they still lack the desirable fully transparent appearance.

The above-described principle is also known from EP-A-0 942 139 which discloses a method for laser welding transparent window panes to a frame, the frame at least at the abutment surfaces absorbing the laser light, this making it necessary to provide the laser light from each side of the frame.

However, for a number of different products it is necessary to establish a weld between only two layers within a product which in its finished state is a multi-layer assembly.

A first example of this kind of product is ostomy pouches that ordinarily consist of two pouch walls welded together along their contour. One of the walls has an aperture which receives material discharged from the stoma. A coupling element, e.g. an adhesive label or a faceplate, is affixed to the pouch wall around the stomal aperture by welding or adhesion. The coupling element permits the detachable fastening of the pouch on the user's body around stoma.

In the production of such ostomy pouches, the starting material used is generally two webs of weldable plastic sheet material that are advanced stepwise through an apparatus with three stations. The first station has a punching tool to produce the apertures in one of the webs, the coupling element being welded onto said web around the apertures at the second station, and the two webs being subsequently brought together and united along a line corresponding to the desired contour of the pouch by means of an annular welding electrode at the third station. The finished pouches may simultaneously be separated from the remaining sheet material.

As the contour welding operation cannot be carried out through the coupling element it is a primary condition in this technique of production that the coupling element be positioned entirely within the contour of the pouch. In many cases, this is completely acceptable. However, in other cases, it means that for production reasons the pouch must be made bigger than otherwise necessary or that the distance from the aperture to the top of the pouch must be increased. The use of a pouch having such increased dimensions can result in the upper part of the pouch pulling away from the user's body as a consequence of the increase in weight when the pouch fills.

According to EP-A-0 045 587, a method of manufacturing ostomy pouches in which an adhesive label or faceplate can extend past part of the pouch contour is suggested. The particular feature of this method consists in that the two pouch walls in a first step are joined by partial contour welding, namely over an area extending from the top edge of the pouch past the region of the weld seam around the aperture. The adhesive label or faceplate is subsequently applied by welding while using a separator member introduced into the partially finished pouch. The separator functions as a base for the pouch wall to which the label is being welded. The contour welding operation is subsequently completed in a second step after withdrawal of the separator member. Although EP-A-0 045 587 discloses a method which is suitable for the manufacture of the desired ostomy pouch, this method is relatively complex using a large number of manufacturing steps as well as special equipment and is thus cost-ineffective.

In the above mentioned example, placement problems of a coupling element such as an adhesive label are discussed, but the same considerations are valid in other cases, e.g. when external components such as filter assemblies with similar dimensional features are to be fixed on a pouch.

Another type of product featuring a multi-layer construction with welds between only two layers within the finished product is ostomy and urine collecting bags with internal valves formed between one or two additional internal sheet-elements.

An example of such a product is known from EP-A-0 106 587 which discloses a drainage bag which incorporates a non-return valve assembly. More particularly, the valve assembly includes at least one baffle positioned intermediate the top and bottom of the bag and extending across the bag from its left side to its right side. Each baffle has an upper portion which is continuously attached to one face of the bag from the left side of the bag to the right side of the bag and a lower portion which is attached to an opposite face of the bag at spaced intervals between the left side of the bag and the right side of the bag. By this construction, at least one opening is formed along the bottom portion of the baffle, the opening or openings being positioned adjacent to the front or back face of the bag so as to permit liquid to flow readily from the top of the bag to the bottom of the bag while inhibiting liquid from flowing from the bottom of the bag to the top of the bag. Although EP-A-0 106 587 discloses the use of a single baffle member, non-return valves can also be formed with two intermediate baffle layers, each attached to a wall of the pouch.

A further type of product featuring a multi-layer construction with welds between only two layers within the finished product is ostomy and urine collecting bags with internal walls attached between the outer front and back walls in order to reduce bulking when the bag is filled. Such a bag as well as methods for the manufacture thereof is disclosed in WO 93/17643.

As follows from the description of the just described two types of bags, such bags comprise at least three layers making up the outer front and back walls and the baffle member/internal wall of the bag, respectively, the inner layer being attached to the outer walls along welding seams.

U.S. Pat. No. 5,165,799 discloses a method in which a curable adhesive is applied, e.g. printed, to selected surface portions of layers in a multi-layer plastic bag. The adhesive is cured by an electron beam curtain emitted across the full width of the bag. Although this method allows for selective bonding of individual portions of layers in a multi-layer construction, the accuracy relies entirely on the positioning of the printed layers prior to curing, this making the method unsuitable for products in which a high degree of precision is required, such as for medical appliances. Further, for some medical appliances, a welded bond may be required.

As appears from the above, it would be desirable if multi-layer assemblies of the described types could be manufactured in a simple, reliable and cost-effective way providing a high degree of precision. Therefore, it is the object of the present invention to provide a method which makes it possible to manufacture an assembly in which a weld is established between only two layers at a given location within a product which in its finished state is a multi-layer assembly, and which circumvents one or more of the above-described drawbacks of the prior art.

SUMMARY OF THE INVENTION

The present invention is based upon the recognition that welds can be established directly between selected layers only of an assembly with multiple layers using a suitable technique. In the context of this application the term "layer" only implies that a "work-piece" is described. Consequently, although for some of the preferred embodiments for the present invention the term "layer" is used to describe thin, foil- or sheet-like materials, the principles of the present invention relates to the assembly of "work-pieces" in general. Further, when in the context of the present invention it is described that a layer is provided with a surface-layer of an absorbent material, this also includes embodiments in which a thin absorbent film-member is positioned on the layer, either attached thereto or loose.

Accordingly, a first aspect of the present invention solves the stated problem by providing a method in which a laser light is directed through an outer layer, allow-transmission of the laser light from its outer surface to at least within the vicinity of its inner surface substantially without any absorption of energy from the laser light, towards a layer comprising an absorbent component, corresponding to a portion thereof, capable of absorbing laser light within a given wavelength range thereby creating a welded area between a surface of the layer comprising the absorbent component and a surface of a layer facing the layer comprising the absorbent component. The absorbent component can be provided either within the bulk of a layer (entirely or partly) or it can be provided as a separate surface-layer on selected portions of one or both surfaces of a layer. The surface-layers could be provided by use of any suitable technique, including painting, printing, coating, co-extruding and the use of separate film member.

By the term "provided within the bulk of a layer" reference is also made to materials which "themselves" act as absorbents.

By providing a layer allowing transmission of laser light there through with a painted or printed absorbent component on a portion only of one or both of its respective surfaces, a given layer can both transmit and absorb laser light in specified areas, this allowing a bond to be placed with great precision within the absorbent area, while at the same time allowing laser light to be transmitted through other portions of the surface thereby creating bonds "deeper" in the multi-layer construction. Further, as the absorbent component may have a visible colour, a more attractive appearance can be achieved.

By use of these principles of manufacture a great variety of different products can be manufactured in which welds are made "within" the product after the initial assembly of the multiple layers.

In a further aspect of the present invention, methods for manufacturing pouches of the types known from EP-A-0 045 587 and EP-A-0 106 587 respectively, and as described above, are provided, as well as pouches comprising features unique to these methods.

In order to provide a welding, the contacting surfaces have to be properly brought into contact with each other using a clamping arrangement. However, as it may require very large forces to ensure proper contact, the surface areas to be welded may advantageously be provided with adhesive means providing an aid in establishing proper contact. In this way the clamping means' main purpose would be to flatten the multi-layer assembly during welding, the intimate contact between the surfaces to be bonded being provided, at least partially, by the adhesive means. The adhesive may be supplied as part of an absorbent coating applied in a desired pattern onto a surface, or it may be applied in a desired pattern onto a generally absorbent surface.

Indeed, in its broadest concept this method provides a general means for assisting in providing contact during contact-requiring procedures.

BRIEF DESCRIPTION OF THE DRAWINGS

The method and apparatus according to the invention are illustrated by the accompanying drawings, where like numerals indicate like elements and in which.

DETAILED DESCRIPTION OF THE INVENTION

Figure 1A:
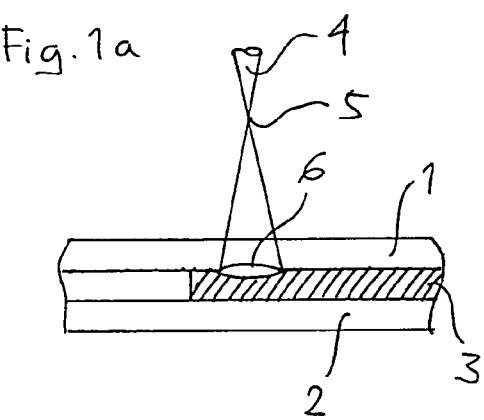
FIGS. 1a and 1b are schematic representations of a first multi-layer assembly, comprising three layers.
Figure 1B:
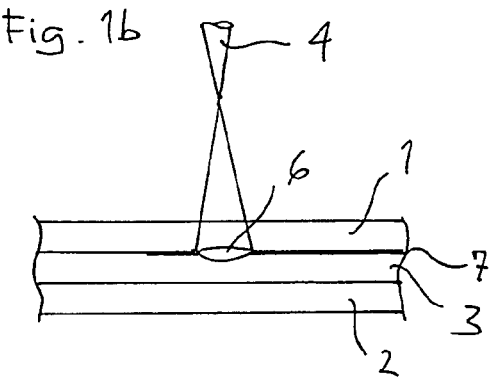

FIGS. 1a and 1b show two variations of a first multi-layer assembly comprising three layers and being manufactured according to the present invention. In FIG. 1a, the multi-layer assembly comprises a first outer translucent layer 1, a second outer layer 2 and an intermediate layer 3 positioned between the first and second layers. The intermediate layer 3 comprises, corresponding to a portion thereof, e.g. on a surface or in the bulk, an absorbent component capable of absorbing laser light within a given wavelength range; this component may either be the material from which the layer is manufactured or it may be an added component such as carbon or a dye mixed into the bulk of the material. Specific materials for use as an added absorbent will be discussed in greater detail below. After the three layers have been positioned on top of each other with the contacting surfaces properly brought into contact with each other by using an appropriate clamping arrangement (not shown but discussed in greater detail below), the assembly is subjected to a laser beam 4 having a wavelength corresponding to the given absorbent chosen and with a beam focus position as indicated by 5. The focus point of the laser beam is shown for illustration only and may be placed higher or lower and even below the objects to be welded according to the work-pieces and laser technology involved. The laser light travels through the first translucent outer layer 1 but when it subsequently travels through the outer portions of layer 3 most proximate to the outer layer, light is absorbed resulting in local heating and thus melting of the components corresponding to the interface between the first outer layer and the intermediate layer. This local melting of the components of the two layers results in the formation of a weld 6 connecting layers 1 and 3.

FIG. 1b shows a similar assembly as FIG. 1a in which the bulk absorbent of the intermediate layer 3 has been replaced by a layer 7 of absorbent material provided (for example painted or printed) on a portion of the surface of intermediate layer 3 facing the outer layer 1, this resulting in a weld being formed between the two layers. Indeed, the absorbent material could also be applied on the inner surface of the outer layer 1 with corresponding effect.

Figure 2A:
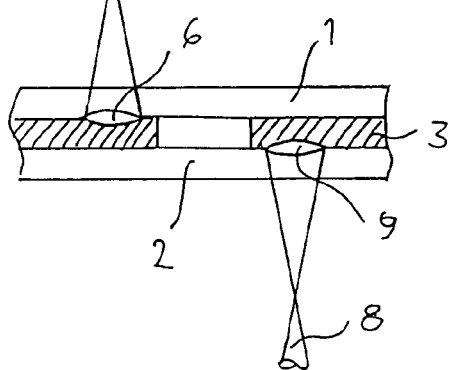
FIGS. 2a and 2b are schematic representations of a second multi-layer assembly, comprising three layers.
Figure 2B:
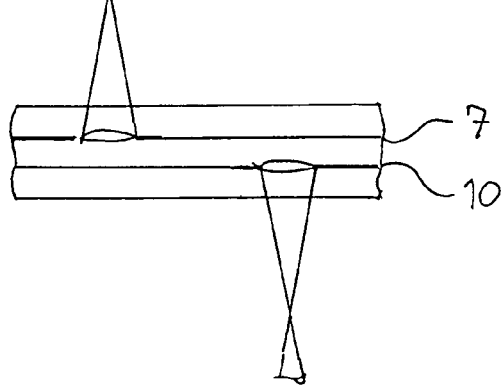

FIGS. 2a and 2b show two variations of a second multi-layer assembly comprising three layers and being manufactured according to the present invention. In FIG. 2a, the multi-layer assembly comprises a first outer translucent layer 1, a second outer translucent layer 2 and an intermediate layer 3 positioned between the first and second layers. The intermediate layer 3 comprises, corresponding to a portion thereof, an absorbent component capable of absorbing laser light within a given wavelength range. After the three layers have been positioned on top of each other with the contacting surfaces properly brought into contact with each other by using an appropriate clamping arrangement (not shown), the assembly is subjected to a first laser beam 4. The laser light travels through the translucent outer layer 1 but when it subsequently travels through the outer portions of layer 3 most proximate to the outer layer, light is absorbed resulting in local heating and thus melting of the components corresponding to the interface between the first outer layer and the intermediate layer. The local melting of the components of the two layers of the components of the two layers results in the formation of a weld 6 connecting layers 1 and 3. Subsequently, or simultaneously if desired, the assembly is subjected to a second laser beam 8. The laser light from the second beam travels through the translucent outer layer 2 but when it subsequently travels through the outer portions of layer 3 most proximate to the second outer layer 2, light is absorbed resulting in local heating and thus the formation of a weld 9 connecting layers 2 and 3.

FIG. 2b shows a similar assembly as FIG. 2a in which the bulk absorbent of the intermediate layer 3 has been replaced by surface-layers 7, 10 of absorbent material provided on portions of the surfaces of intermediate layer 3 facing the outer layers 1, 2 respectively, this resulting in welds 6, 9 being formed between the two layers. Indeed, the absorbent material could also be applied on the inner surface of the respective outer layers 1, 2 with corresponding effect. As described above, the surface-layers could be provided using any suitable technique.

Figure 3:
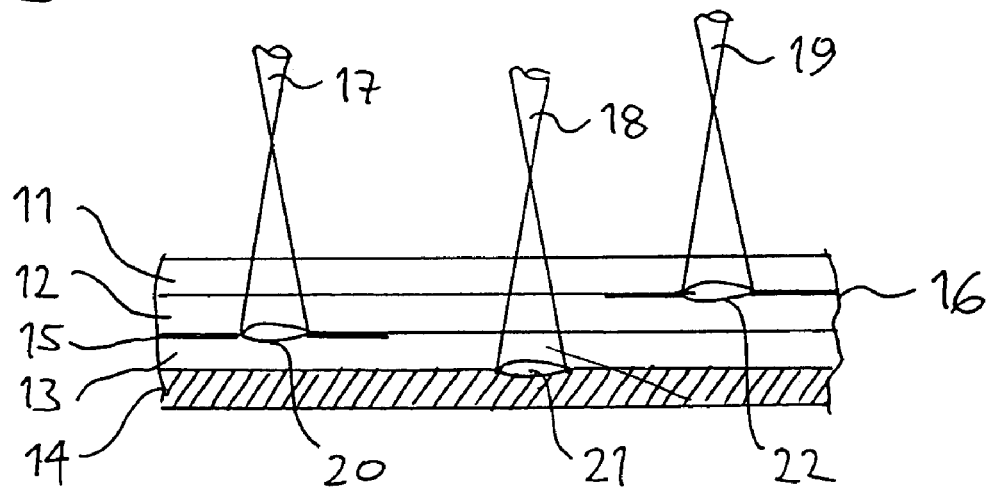
FIG. 3 is a schematic representation of a third multi-layer assembly, comprising four layers.

FIG. 3 shows a third multi-layer assembly comprising four layers and being manufactured according to the present invention. The multi-layer assembly comprises a first outer translucent layer 11, a second outer layer 14, a first intermediate principally translucent layer 12 positioned against the first outer layer 11, and a second principally translucent intermediate layer 13 positioned between the second outer layer and the first intermediate layer. The second outer layer 14 comprises an absorbent bulk component capable of absorbing laser light within a given wavelength range; this component may as for the embodiments of FIGS. 1 and 2 be either the material from which the layer is manufactured or it may be an added component. Instead of a bulk component the second outer layer could also be provided with an absorbent layer on its surface facing the second intermediate layer. The second intermediate layer 13 is provided with a surface-layer 15 of an absorbent material on a portion of the surface thereof facing the first intermediate layer 12, and the first intermediate layer 12 is provided with a surface-layer 16 of an absorbent material on a portion of the surface thereof facing the first outer layer 11. Indeed, surface-layers 15, 16 could also be provided on the correspondingly facing surfaces.

After the four layers have been positioned on top of each other with the contacting surfaces properly brought into contact with each other by using an appropriate clamping arrangement (not shown), the assembly is subjected to a first laser beam 17. The laser light travels through the translucent layers 11, 12 but when it subsequently travels through the outer portions of second intermediate layer 13 most proximate to the first intermediate layer 12, light is absorbed resulting in local heating and thus melting of the components corresponding to the interface between the first and second intermediate layers 12, 13 resulting in the formation of a first weld 20 connecting layers 12 and 13. Subsequently, or simultaneously if desired, the assembly is subjected to a second laser beam 18. The laser light from the second beam travels through the translucent layers 11, 12, 13 but when it subsequently travels through the outer portions of the second outer layer 14 most proximate to the second intermediate layer 13, light is absorbed resulting in local heating and thus the formation of a second weld 21 connecting layers 13 and 14. Subsequently, or simultaneously if desired, the assembly is subjected to a third laser beam 19. The laser light travels through the outer translucent layer 11 but when it subsequently travels through the outer portions of the first intermediate layer 12 most proximate to the first outer layer 11, light is absorbed resulting in local heating and thus melting of the components corresponding to the interface between the first outer layer and the first intermediate layer 12 resulting in the formation of a third weld 22 connecting layers 11 and 12.

Although three laser light sources 17, 18, 19 are shown, the laser light for all three welds could advantageously be provided by a single laser beam with either a variable or fixed focus; the latter would be appropriate when the layers are relatively thin. Further, to provide spot welding at different points or longitudinal welding seams, the position of the laser beam should be controlled correspondingly. Indeed, further layers could be added and it thus clearly appears that by this method very complicated assemblies can be manufactured in a convenient and effective way.

Figure 4:
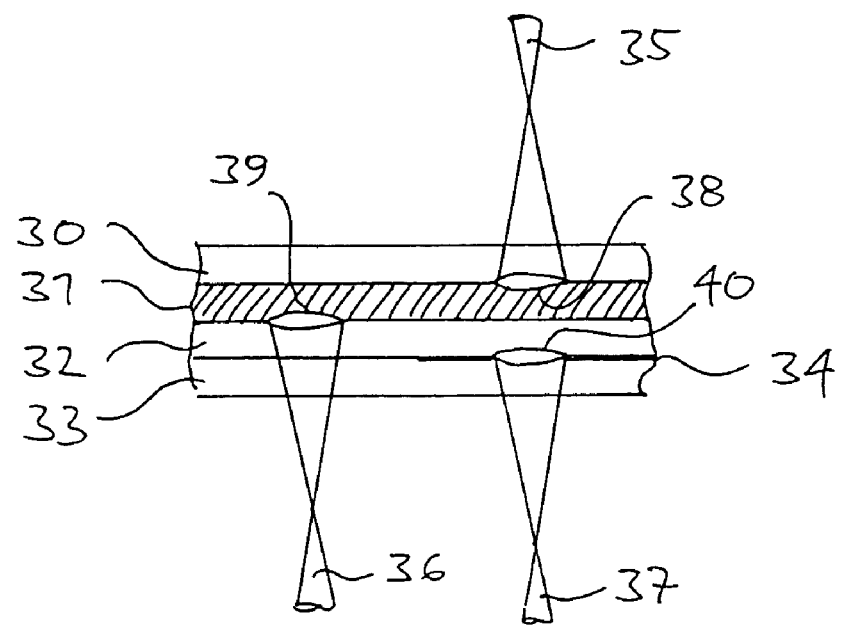
FIG. 4 is a schematic representation of a fourth multi-layer assembly, comprising four layers.

FIG. 4 shows a fourth multi-layer assembly comprising four layers and being manufactured according to the present invention. The multi-layer assembly comprises a first outer translucent layer 30, a second outer translucent layer 33, a first intermediate layer 31 positioned against the first outer layer 30, and a second primarily translucent intermediate layer 32 positioned between the second outer layer 33 and the first intermediate layer 31. The first intermediate layer 31 comprises an absorbent component capable of absorbing laser light within a given wavelength range; this component may as for the embodiments of FIGS. 1, 2 and 3 be either the material from which the layer is manufactured or it may be an added component. Instead of a bulk component the first intermediate layer could also be provided with an absorbent layer on both its surfaces. The second intermediate layer 32 is provided with a surface-layer 34 of an absorbent material on a portion of the surface thereof facing the second outer layer 33. Indeed, surface-layer 34 could also be provided on the correspondingly facing surface of the second outer layer.

After the four layers have been positioned on top of each other with the contacting surfaces properly brought into contact with each other by using an appropriate clamping arrangement (not shown), the assembly is subjected to a first laser beam 35. The laser light travels through the translucent outer layer 30 but when it subsequently travels through the outer portions of first intermediate layer 31 most proximate to the first outer layer 30, light is absorbed resulting in local heating and thus melting of the components corresponding to the interface between the first outer layer 30 and the first intermediate layer 31 resulting in the formation of a first weld 38 connecting layers 30 and 31. Subsequently, or simultaneously if desired, the assembly is subjected to a second laser beam 36. The laser light from the second beam travels through the translucent layers 33, 32 but when it subsequently travels through the outer portions of the first intermediate layer 31 most proximate to the second intermediate layer 32, light is absorbed resulting in local heating and thus the formation of a second weld 39 connecting layers 31 and 32. Subsequently, or simultaneously if desired, the assembly is subjected to a third laser beam 37. The laser light travels through the second outer translucent layer 33 but when it subsequently travels through the outer portions of the second intermediate layer 32 most proximate to the second outer layer 33, light is absorbed resulting in local heating and thus melting of the components corresponding to the interface between the second outer layer 33 and the second intermediate layer 32 resulting in the formation of a third weld 44 connecting layers 33 and 32.

As with the embodiment of FIG. 3, a single laser advantageously provides second and third laser beams 36, 37.

As stated in the introduction, opaque materials or carbon black as an added absorbent have been used for a number of years in order to provide materials which will heat when subjected to laser light; however, due to the lack of transparency of the materials, this method has not found great acceptance within the technical field of medical devices.

According to WO 00/20157 the above drawbacks have been eliminated or reduced by a method in which two workpieces are welded together over a joint region by exposing the region to incident radiation, e.g. laser light, having a wavelength outside the visible range, and where a radiation absorbing material at the joint region which has an absorption band matched to the wavelength of the incident radiation so as to absorb the incident radiation and generate heat for the melting/welding process, the absorption band being substantially outside the visible range so that the material does not affect the appearance of the joint region or the work-pieces in visible light. This method is preferred for use with the methods of the present invention.

In a paper titled "use of infrared dyes for transmission laser welding in plastics" from Antec 2000, Conference Proceedings Vol. 1, a conference for The society of plastic Engineers which took place May 11 to 17, 2000 in Orlando, Fla., the principles of the above referred method is considered in further detail. In this paper the requirements for the selection of near-infrared dyes for laser welding are listed: a narrow absorption band near the laser wavelength with a high molar absorption coefficient, little if any absorption in the region 400-700 nm, good solubility in the host material, good stability towards the incorporation method used, and should not degrade to coloured by-products. Examples of dyes which fulfil these requirements are listed as the cyanine dyes, the squarylium dyes and the croconium dyes. The lasers to be used for described method are Nd:YAG with 1064 nm wavelength and diode lasers with 800-1100 nm wavelength. The paper also lists a number of methods by which the dyes can be incorporated. The above listed properties, materials and lasers are preferred for use with the methods of the present invention.

Figure 5:
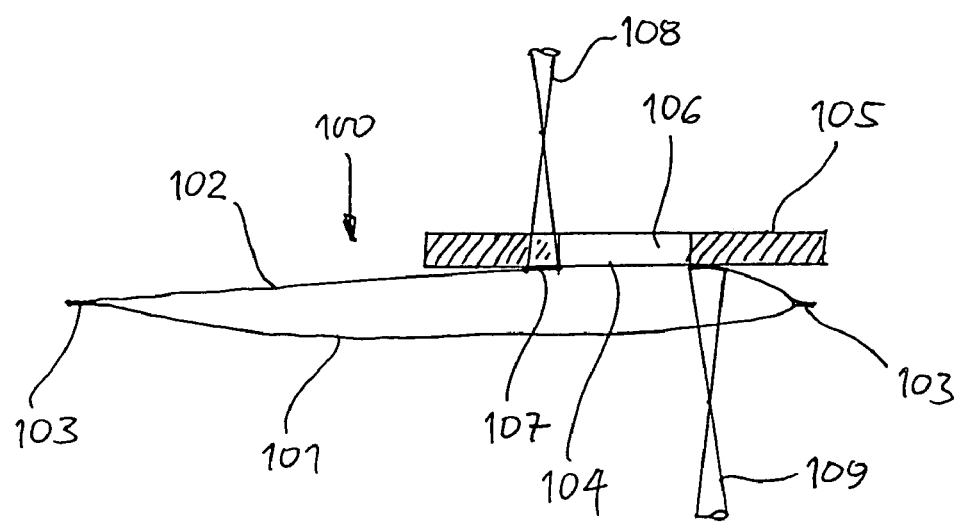
FIG. 5 illustrates a first multi-layer construction which can advantageously be manufactured by use of the method of the present invention.

As mentioned above, after the different layers have been positioned on top of each other, the contacting surfaces have to be properly brought into contact with each other using a clamping arrangement. In the above-referred Antec 2000 paper, FIG. 5 shows a diagram in which two workpieces are clamped using traditional clamping tools located outside the region to be joined by welding, i.e. in order not to interfere with the laser beam. However, by using the principles of the present invention, clamping can be provided across a large area of the multi-layer assembly to be welded by using relatively rigid, plate-like clamping members which generally cover the whole of the area within which welds are to be placed and which allow transmission of the laser light therethrough. The clamping members comprise at least one resilient surface facing the assembly, so that different thicknesses of the multi-layer assembly will be clamped with substantially the same contact pressure. The clamping pressure may be established by forces applied on the outside of the clamp or it may be established by sealing of the edges of the clamp and evacuating the space between the inner clamp surfaces facing the multi-layer assembly. Such a clamping method provides a number of advantages as it is easy to position irrespective of the actual location of the welds to be made, and it is very flexible under varying production runs as the location of the welding locations can be changed without any modifications to the transparent clamping element. Further, clamping over the whole area of the multi-layer assembly reduces the problems with wrinkling when the clamping means are brought in contact with the assembly. Indeed, if the assembly is to be welded using laser light from both sides, transparent clamping means should be used on both sides.

As described in the introductory portion, it may require very large forces to secure proper contact. Therefore, the surface areas to be welded may advantageously be provided with adhesive means providing an aid in establishing proper contact. In this way the clamping means main purpose would be to flatten the multi-layer assembly during welding, the intimate contact between the surfaces to be bonded being provided, at least partially, by the adhesive means.

With reference to FIG. 5 a first preferred method of manufacturing an ostomy collecting bag using the method of the present invention will be described. As mentioned above with reference to EP-A-0 045 587, it has been difficult to manufacture ostomy pouches in which the adhesive label or faceplate can extend past part of or even past the whole pouch contour.

First a pouch 100 is provided in which outer pouch wall 101 and inner pouch wall 102 in a first step are contour welded together by any suitable method along the edges thereof to form a contour seam 103. The inner wall comprises an opening 104 around which a coupling component 105, e.g. an adhesive label, with a corresponding opening 106 is positioned. After the coupling component has been properly clamped onto the pouch the coupling component is welded to the inner pouch wall along weld 107 using the method of the present invention. FIG. 5 illustrates two different methods of attaching the coupling component. In case the coupling component 105 is manufactured from translucent materials an absorbent component is provided at the region to be joined, i.e. corresponding to the circumferential edges of openings 104, 106. The absorbent material can be provided in bulk in the inner pouch wall or it can be provided on one of the surfaces to be joined, i.e. either the surface of the coupling component facing the inner pouch wall or the surface of the inner pouch wall facing the coupling component. Preferably, the absorbent material is provided corresponding to a portion only of the surface of either the coupling element or the pouch wall. A laser beam 108 is then directed across the area to be welded resulting in weld 107. In the alternative, when the outer pouch wall 101 is translucent to laser light, the absorbent material can be provided in bulk in the coupling component, preferably corresponding to only a portion of the coupling element, or, as above, it can be provided on one of the surfaces to be joined. A laser beam 109 is then directed across the area to be welded resulting in weld 107.

In the above described preferred embodiment a coupling component such as an adhesive label or a coupling ring is used as example; however, instead of a coupling component a wide variety of other components could be attached using the disclosed method, e.g. when filter assemblies with similar dimensional features are to be fixed on a pouch.

Figure 6:
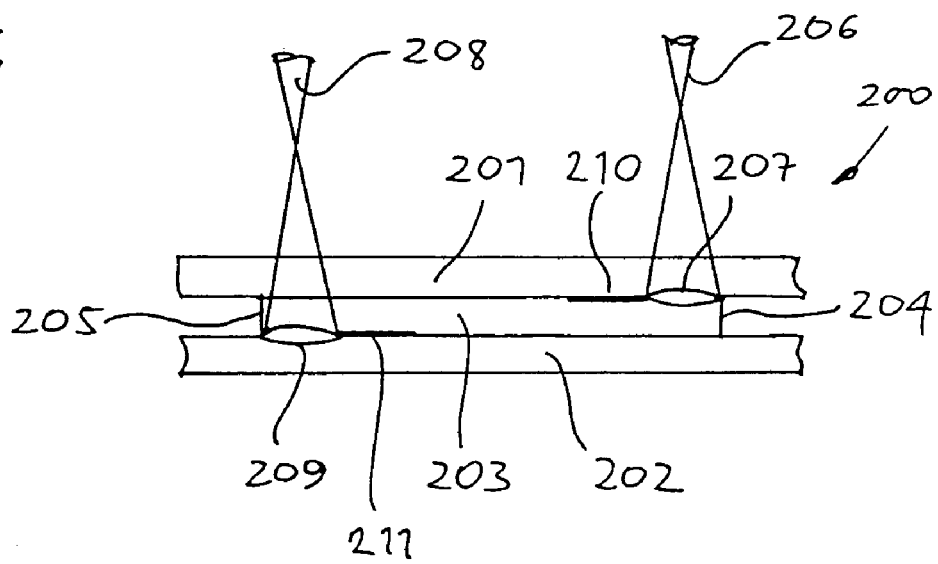
FIG. 6 illustrates in part a second multi-layer construction which can advantageously be manufactured by use of the method of the present invention.

With reference to FIG. 6 a second preferred method of manufacturing an ostomy collecting bag using the method of the present invention will be described. As mentioned above with reference to EP-A-0 106 587 and WO 93/17643 it is often desirable to attach an intermediate member to the front and rear walls of a collecting bag, thus creating a member spanning between the walls, for example to create a valve or a supporting structure.

First a laminate 200 is provided comprising first pouch wall 201 and second pouch wall 202 as well an intermediate baffle layer with upper and lower edges 204, 205 interposed there between. At this point the three layers may have been contour welded together by any suitable method along their edges to form a pouch; the baffle member may have been attached to the walls corresponding to the ends thereof, i.e. the portions directed in and outwards relative to the plane of the figure. The first pouch wall 201 and the baffle member 203 are predominantly made of translucent material allowing laser light to pass through to the regions to be joined. Absorbent material 210, 211 is provided corresponding to the regions to be joined, i.e. corresponding to the area between the first pouch wall 201 and the baffle member along the upper end (204) of the latter, as well as the area between the second pouch wall 202 and the baffle member along the lower edge of the latter. In this way the absorbent material 210, 211 is provided in a non-overlapping pattern allowing laser light to be used from one side only. As described above with reference to FIG. 5, the absorbent material can be provided on either of the surfaces to be joined. Thereafter the laminate is properly clamped and a first laser beam 206 is directed through the first pouch wall 201 to thereby create a first joined region 207, and a second laser beam 208 is directed through the first pouch wall 201 and the baffle member 203 to thereby create a second joined region 209. Depending on the specific purpose of the baffle member, e.g. to function as a valve or a support member, the joined regions 207, 209 may run either fully or partially along the upper 204 and lower 205 edges of the baffle member. If the baffle member is used to form a valve, the baffle member will typically be joined to the first wall along the length of the upper edge whereas the lower edge will be left with one or more interruptions to allow liquid to pass through, this as illustrated for example in FIGS. 1 and 2 of EP-A-0 106 587.

Figure 7:
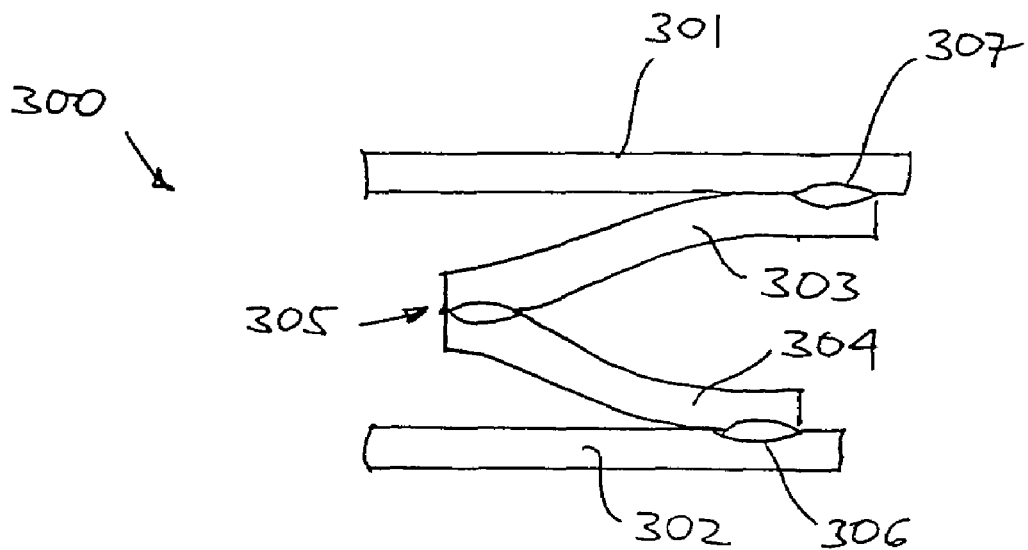
FIG. 7 illustrates in part a third multi-layer construction which can advantageously be manufactured by use of the method of the present invention.
Figure 8:
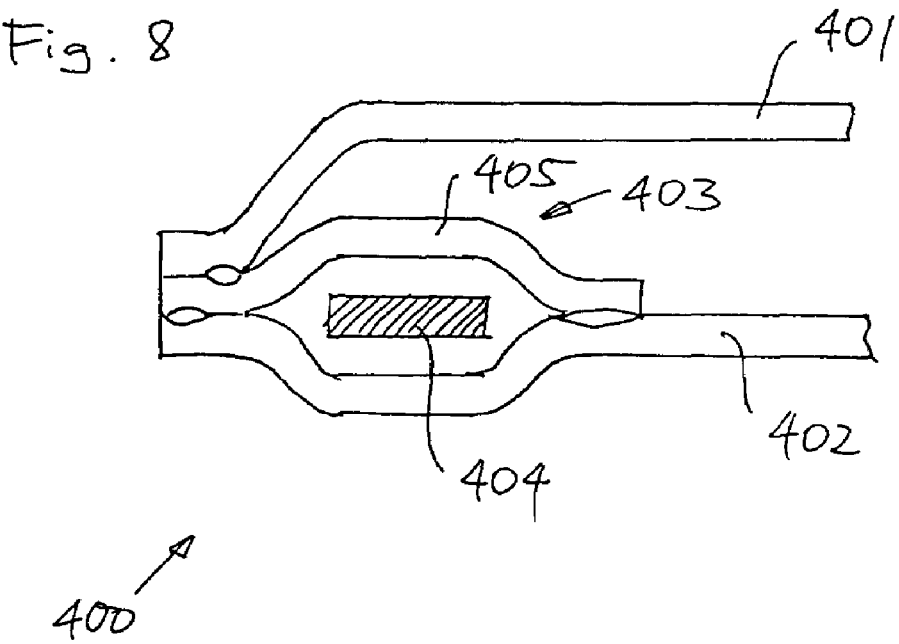
FIG. 8 illustrates in part a fourth multi-layer construction which can advantageously be manufactured by use of the method of the present invention.

FIGS. 7 and 8 show further embodiments of multi-layer constructions which can advantageously be manufactured by use of the methods of the present invention. FIG. 7 shows in part a four-layered pouch assembly 300 comprising first and second outer walls 301, 302 and a valve member 305 formed between first and second intermediate layers 303, 304. It is to be noted that the weld 307 has been displaced slightly relative to the weld 306, this allowing the welds to be formed with a laser from the same side. FIG. 8 shows in partial a three-layered pouch assembly 400 comprising first and second outer walls 401, 402 and a pocket 403 for a filter 404 formed between an intermediate layer 505 and the second outer wall 402. It is again to be noted that the two welds to the right in the drawing have been displaced slightly relative to each other. Having regard to the detailed description of the embodiments of FIGS. 5 and 6 it will be clear to the skilled person how to apply the methods of the present invention to these embodiments also, i.e. providing the absorbent material at the relevant locations and directing the laser light through the corresponding layers.

It will be understood that the embodiments described herein are merely exemplary and that a person skilled in the art may make many variations and modifications without departing from the scope of the invention.

What is claimed is:

1. A method for forming a weld between two layers within a multi-layer assembly, comprising the steps of:
   providing a multi-layer assembly of individual layers, including a first outer layer with first outer and inner surfaces, a second outer layer with second outer and inner surfaces, and at least one intermediate layer positioned between the first and second outer layers, said first outer layer having a first region including an absorbent component capable of absorbing laser light within a given wavelength range and a second region having no absorbent component, said second outer layer having a third region including an absorbent component, said third region overlapping the second region, and at least one of the first and second outer layers allowing transmission of the laser light from its outer surface to within the vicinity of its inner surface substantially without any absorption of energy from the laser light;

directing laser light within the given wavelength range through the first outer layer towards the absorbent component in the first region, thereby creating a first welded area between a surface of the first outer layer and a surface of a layer facing the first region; and directing laser light within the given wavelength range through the first outer layer and through the second region towards the absorbent component in the third region, thereby creating a second welded area between a surface of the second outer layer and a surface of a layer facing the third region.

2. The method according to claim 1, including providing a first layer with an absorbent component within the bulk thereof, and providing a second layer with an absorbent component on a portion of a surface.

3. The method according to claim 1, wherein the absorbent component is selected from the group consisting of the cyanine dyes, the squarylium dyes and the croconium dyes, and the method includes using a laser having a wavelength within the 800-1100 nm wavelength.

4. The method according to claim 1 adapted for attaching an intermediate member within a pouch assembly, further comprising the steps of:

providing a pouch assembly including a first pouch wall and a second pouch wall, each having inner and outer surfaces, and an intermediate member arranged between the walls and having first and second surfaces, an absorbing component capable of absorbing laser light within a given wavelength range being provided at a region to be joined between the intermediate member and at least one of the pouch walls, and at least one of the pouch walls allowing transmission of the laser light from its outer surface to within the vicinity of its inner surface substantially without any absorption of energy from the laser light;

directing laser light within the given wavelength range to the region(s) to be joined; and thereby creating a welded area between the intermediate member and the at least one pouch wall.

5. The method according to claim 4, wherein a first region to be joined is defined between a portion of the first surface of the intermediate member and the inner surface of the first pouch wall, and a second region to be joined is defined between a portion of the second surface of the intermediate member and the inner surface of the second pouch wall, the method further including providing the absorbing component at the first and second regions in a non-overlapping pattern.

6. The method according to claim 5, wherein the first pouch wall allows transmission of the laser light therethrough corresponding to the first region to be joined, and the first pouch wall and the intermediate member allow transmission of the laser light therethrough corresponding to the second region to be joined, said method including directing laser light towards the first and second regions through the first pouch wall.

7. The method according to claim 4, wherein a first region to be joined is defined between a portion of the first surface of the intermediate member and the inner surface of the first pouch wall, and a second region to be joined is defined between a portion of the second surface of the intermediate member and a surface of a further intermediate member, the method including providing the absorbing component at the first and second regions in a non-overlapping pattern.

8. The method according to claim 7, wherein the first pouch wall allows transmission of the laser light therethrough corresponding to the first region to be joined, and the first pouch wall and the intermediate member allow transmission of the laser light therethrough corresponding to the second region to be joined, said method including directing laser light towards the first and second regions through the first pouch wall.

9. The method according to claim 4, wherein the first and second pouch walls have circumferential edges at their peripheries, the method including confining an edge of the intermediate member within the circumferential edges and with a distance thereto corresponding to at least one location.

10. A method for forming a weld between two layers within a multi-layer assembly, comprising the steps of:

providing a multi-layer assembly of individual layers including a first outer layer with first outer and inner surfaces, a second outer layer with second outer and inner surfaces, and at least one intermediate layer positioned between the first and second outer layers, the intermediate layer allowing transmission of laser light therethrough and being provided with an absorbent component capable of absorbing laser light within a given wavelength range on a portion of both of its respective surfaces in a non-overlapping pattern, at least one of the outer layers allowing transmission of the laser light from its outer surface to within the vicinity of its inner surface substantially without any absorption of energy from the laser light;

directing laser light within the given wavelength range through at least one of the outer layers towards the absorbent component; and thereby creating a welded area between a surface of the layer having the absorbent component and a surface of a layer facing the layer having the absorbent component.

11. The method according to claim 10, providing a first layer with an absorbent component within the bulk thereof, and providing a second layer with an absorbent component on a portion of a surface.

12. The method according to claim 10, wherein the absorbent component is selected from the group consisting of the cyanine dyes, the squarylium dyes and the croconium dyes, and the method includes using a laser having a wavelength within the 800-1100 nm wavelength.

13. The method according to claim 10 adapted for attaching an intermediate member within a pouch assembly, comprising the steps of:

providing a pouch assembly including a first pouch wall and a second pouch wall, each having inner and outer surfaces, and an intermediate member arranged between the walls and having first and second surfaces, an absorbing component capable of absorbing laser light within a given wavelength range being provided at a region to be joined between the intermediate member and at least one of the pouch walls, and at least one of the pouch walls allowing transmission of the laser light from its outer surface to within the vicinity of its inner surface substantially without any absorption of energy from the laser light;

directing laser light within the given wavelength range to the region(s) to be joined; and thereby creating a welded area between the intermediate member and the at least one pouch wall.

14. The method according to claim 13, wherein a first region to be joined is defined between a portion of the first surface of the intermediate member and the inner surface of the first pouch wall, and a second region to be joined is defined between a portion of the second surface of the intermediate member and the inner surface of the second pouch wall, the method including providing the absorbing component at the first and second regions.

15. The method according to claim 14, wherein the first pouch wall allows transmission of the laser light therethrough corresponding to the first region to be joined, and the first pouch wall and the intermediate member allow transmission of the laser light therethrough corresponding to the second region to be joined, the method including directing laser light towards the first and second regions through the first pouch wall.

16. The method according to claim 13, wherein a first region to be joined is defined between a portion of the first surface of the intermediate member and the inner surface of the first pouch wall, and a second region to be joined is defined between a portion of the second surface of the intermediate member and a surface of a further intermediate member, the method including providing the absorbing component at the first and second regions.

17. The method according to claim 16, wherein the first pouch wall allows transmission of the laser light therethrough corresponding to the first region to be joined, and the first pouch wall and the intermediate member allow transmission of the laser light therethrough corresponding to the second region to be joined, the method including directing laser light towards the first and second regions through the first pouch wall.

18. The method according to claim 13, wherein the first and second pouch walls have circumferential edges at their peripheries, the method including confining an edge of the intermediate member within the circumferential edges and with a distance thereto corresponding to at least one location.

19. A multi-layer assembly, comprising:
a first outer layer with first outer and inner surfaces;
a second outer layer with second outer and inner surfaces; and
at least one intermediate layer positioned between the first and second layers,
said first outer layer having a first region including an absorbent component capable of absorbing laser light within a given wavelength range and a second region having no absorbent component;
said second outer layer having a third region including an absorbent component capable of absorbing laser light within a given wavelength, the third region overlapping with the second region;
at least one of the outer layers allowing transmission of the laser light from its outer surface to within the vicinity of its inner surface substantially without any absorption of energy from the laser light;
other layers, if any, allowing transmission of the laser light corresponding to the regions;
a first weld formed between a surface of the first region and a surface of a layer facing the first layer, the first weld corresponding to the first region; and
a second weld formed between a surface of the third region and a surface of a layer facing the second layer, the second weld corresponding to the third region.

20. The multi-layer assembly according to claim 19, wherein a first layer is provided with an absorbent component within the bulk thereof, and a second layer is provided with an absorbent component on a portion of a surface.

21. The multi-layer assembly according to claim 19, wherein the absorbent component is selected from the group consisting of the cyanine dyes, the squarylium dyes and the croconium dyes.

22. The multi-layer assembly according to claim 19, further comprising:
a first pouch wall and a second pouch wall, each having inner and outer surfaces, and an intermediate member arranged between the pouch walls and having first and second surfaces;
an absorbing component capable of absorbing laser light within a given wavelength range being provided at a region between the intermediate member and at least one of the pouch walls;
at least one of the pouch walls allowing transmission of the laser light from its outer surface to within the vicinity of inner surface substantially without any absorption of energy from the laser light; and
a weld formed between the intermediate member and the at least one pouch wall corresponding to the region having the absorbing component.

23. The multi-layer assembly according to claim 22, wherein a first region is defined between a portion of the first surface of the intermediate member and the inner surface of the first pouch wall, and a second region is defined between a portion of the second surface of the intermediate member and the inner surface of the second pouch wall, the absorbing component being provided at the first and second regions in a non-overlapping pattern.

24. The multi-layer assembly according to claim 23, wherein the first pouch wall allows transmission of the laser light therethrough corresponding to the first region, and the first pouch wall and the intermediate member allow transmission of the laser light therethrough corresponding to the second region.

25. The multi-layer assembly according to claim 22, wherein a first region is defined between a portion of the first surface of the intermediate member and the inner surface of the first pouch wall, and a second region is defined between a portion of the second surface of the intermediate member and a surface of a further intermediate member, the absorbing component being provided at the first and second regions.

26. The multi-layer assembly according to claim 25, wherein the first pouch wall allows transmission of the laser light therethrough corresponding to the first region, and the first pouch wall and the intermediate member allow transmission of the laser light therethrough corresponding to the second region.

27. The multi-layer assembly according to claim 22, wherein the first and second pouch walls have circumferential edges at the peripheries thereof, an edge of the intermediate member being confined within the circumferential edges and with a distance thereto corresponding to at least one location.

28. A multi-layer assembly, comprising:
a first outer layer with first outer and inner surfaces;
a second outer layer with second outer and inner surfaces;
at least one intermediate layer positioned between the first and second layers, the intermediate layer allowing transmission of laser light therethrough and being provided with an absorbent component capable of absorbing laser light within a given wavelength range on a portion of both of its respective surfaces in a non-overlapping pattern;
at least one of the outer layers allowing transmission of the laser light from its outer surface to within the vicinity of its inner surface substantially without any absorption of energy from the laser lights; and a weld formed between a surface of the intermediate layer having the absorbent component and a surface of a layer facing the layer having the absorbent component.

29. The multi-layer assembly according to claim 28, wherein a first layer is provided with an absorbent component within the bulk thereof, and a second layer is provided with an absorbent component on a portion of a surface.

30. The multi-layer assembly according to claim 28, wherein the absorbent component is selected from the group consisting of the cyanine dyes, the squarylium dyes and the croconium dyes.

31. The multi-layer assembly according to claim 28, further comprising:
   a first pouch wall and a second pouch wall, each having inner and outer surfaces, and an intermediate member arranged between the pouch walls and having first and second surfaces;
   an absorbing component capable of absorbing laser light within a given wavelength range being provided at a region between the intermediate member and at least one of the pouch walls;
   at least one of the pouch walls allowing transmission of the laser light from its outer surface to within the vicinity of inner surface substantially without any absorption of energy from the laser light; and
   a weld formed between the intermediate member and the at least one pouch wall corresponding to the region having the absorbing component.

32. The multi-layer assembly according to claim 31, wherein a first region is defined between a portion of the first surface of the intermediate member and the inner surface of the first pouch wall, and a second region is defined between a portion of the second surface of the intermediate member and the inner surface of the second pouch wall, the absorbing component being provided at the first and second regions.

33. The multi-layer assembly according to claim 32, wherein the first pouch wall allows transmission of the laser light therethrough corresponding to the first region, and the first pouch wall and the intermediate member allow transmission of the laser light therethrough corresponding to the second region.

34. The multi-layer assembly according to clam 31, wherein a first region is defined between a portion of the first surface of the intermediate member and the inner surface of the first pouch wall, and a second region is defined between a portion of the second surface of the intermediate member and a surface of a further intermediate member, the absorbing component being provided at the first and second regions.

35. The multi-layer assembly according to claim 34, wherein the first and second pouch walls have circumferential edges at the peripheries thereof, an edge of the intermediate member being confined within the circumferential edges and with a distance thereto corresponding to at least one location.

36. The multi-layer assembly according to claim 31, wherein the first and second pouch walls have circumferential edges at the peripheries thereof, an edge of the intermediate member being confined within the circumferential edges and with a distance thereto corresponding to at least one location.

* * * * *

UNITED STATES PATENT AND TRADEMARK OFFICE
CERTIFICATE OF CORRECTION

Page 1 of 1

PATENT NO. : 7,572,492 B2
APPLICATION NO. : 11/826266
DATED : August 11, 2009
INVENTOR(S) : Bager et al.

It is certified that error appears in the above-identified patent and that said Letters Patent is hereby corrected as shown below:

Title Page;

On the front page of the patent:

Change "(22) Filed: Jul. 13, 2007" to --(22) PCT Filed: Jun. 27, 2001--

After item (22) add:

--(86) PCT No.: PCT/DK01/00449

§371 (c)(1),
(2), (4) Date: Dec. 19, 2002

(87) PCT Pub. No.: WO02/00144

PCT Pub. Date: Jan. 3, 2002--

After item (65) add:

--(30) Foreign Application Priority Data
Jun. 28, 2000 (DK) ........... PA 2000 01005--

Signed and Sealed this
Twenty-third Day of August, 2011

David J. Kappos
*Director of the United States Patent and Trademark Office*